(12) United States Patent
Daniel et al.

(10) Patent No.: US 8,378,156 B2
(45) Date of Patent: Feb. 19, 2013

(54) PROCESS FOR THE CONVERSION OF ALCOHOL (S) INTO ALCOHOL (S) WITH INCREASED CARBON-CHAIN

(75) Inventors: Berian John Daniel, Beverley (GB); Benjamin Patrick Gracey, Hull (GB); John Glenn Sunley, Cottingham (GB)

(73) Assignee: BP P.L.C., London (GB)

( * ) Notice: Subject to any disclaimer, the term of this patent is extended or adjusted under 35 U.S.C. 154(b) by 248 days.

(21) Appl. No.: 12/735,099

(22) PCT Filed: Dec. 12, 2008

(86) PCT No.: PCT/GB2008/004102
§ 371 (c)(1),
(2), (4) Date: Jun. 16, 2010

(87) PCT Pub. No.: WO2009/077726
PCT Pub. Date: Jun. 25, 2009

(65) Prior Publication Data
US 2010/0317900 A1    Dec. 16, 2010

(30) Foreign Application Priority Data
Dec. 17, 2007  (EP) .................................... 07254901

(51) Int. Cl.
*C07C 29/136* (2006.01)
(52) U.S. Cl. ......... 568/884; 568/885; 568/877; 568/907
(58) Field of Classification Search .................. 568/884, 568/885, 877, 907
See application file for complete search history.

(56) References Cited

U.S. PATENT DOCUMENTS

| 4,447,661 A | * | 5/1984 | Hoshiyama et al. .......... 568/882 |
| 4,454,358 A | | 6/1984 | Kummer et al. |
| 4,831,060 A | | 5/1989 | Stevens et al. |
| 5,364,979 A | * | 11/1994 | Radlowski et al. .......... 568/697 |
| 5,414,161 A | * | 5/1995 | Uhm et al. .................... 568/885 |
| 2006/0252959 A1 | | 11/2006 | Cheung et al. |

FOREIGN PATENT DOCUMENTS

| DE | 28 18 831 | 11/1978 |
| WO | 2007/117590 | 10/2007 |

OTHER PUBLICATIONS

International Search Report for PCT/GB2008/004102, mailed Feb. 10, 2009.
Written Opinion of the International Searching Authority for PCT/GB2008/004102, mailed Feb. 10, 2009.

* cited by examiner

*Primary Examiner* — Brian J Davis
(74) *Attorney, Agent, or Firm* — Nixon & Vanderhye (57) ABSTRACT

Process for homologation of alcohol(s), by 1 introducing alcohol(s) into an etherification unit to produce alkyl ether(s), 2, introducing at least a part of the alkyl ether(s) from step 1, together with CO and optionally $H_2$, into a carbonylation unit, in the presence of an acidic homogeneous or heterogeneous carbonylation catalyst, to produce alkyl ester(s), and 3, introducing at least a part of the alkyl ester(s) from step 2, together with $H_2$, into a hydrogenation unit, to produce homologated alcohol(s). Optionally, at least a part of the homologated alcohol(s) from step 3 is recycled into the etherification unit of step 1. Alcohol(s) from the hydrogenation unit of step 3 are recovered.

18 Claims, 1 Drawing Sheet

US 8,378,156 B2

PROCESS FOR THE CONVERSION OF ALCOHOL (S) INTO ALCOHOL (S) WITH INCREASED CARBON-CHAIN

This application is the U.S. national phase of International Application No. PCT/GB2008/004102, filed 12 Dec. 2008, which designated the U.S. and claims priority to European Application No. 07254901.7, filed 17 Dec. 2007, the entire contents of each of which are hereby incorporated by reference.

The present invention relates to a process for the conversion of alcohol(s) into higher alcohol(s). The present invention also relates to a process for the production of alcohols from synthesis gas In particular, the present invention relates to the production of an alcohol(s) from a carbonaceous feedstock; wherein the carbonaceous feedstock is first converted to synthesis gas which is then converted to alkyl carboxylate ester(s) which is then hydrogenated to produce alcohol(s).

BACKGROUND OF THE INVENTION

In recent years increased use and demand for alcohols such as methanol, ethanol and higher alcohols has led to a greater interest in processes relating to alcohol production. The said alcohols may be produced by the fermentation of, for example, sugars and/or cellulosic materials.

Alternatively alcohols, such as ethanol, may be produced from synthesis gas. Synthesis gas refers to a combination of $H_2$ and carbon oxides produced in a synthesis gas plant from a carbon source such as natural gas, petroleum liquids, biomass and other carbonaceous materials including coal, recycled plastics, municipal wakes, or any organic material. Thus, alcohol and alcohol derivatives may provide non-petroleum based routes for the production of valuable chemicals and fuels.

Generally, the production of alcohols, for example methanol, takes place via three process steps: synthesis gas preparation, methanol synthesis, and methanol purification. In the synthesis gas preparation step, an additional stage may be employed whereby the feedstock is treated, e.g. the feedstock is purified to remove sulphur and other potential catalyst poisons prior to being converted into synthesis gas. This treatment can also be conducted after synthesis gas preparation; for example, when coal or biomass is employed.

The reaction to produce alcohol(s) from synthesis gas is generally exothermic. The formation of $C_2$ and $C_{2+}$ alcohols is believed to proceed via the formation of methanol for modified methanol catalysts and cobalt molybdenum sulphide catalysts. However, the production of methanol is equilibrium-limited and thus requires high pressures in order to achieve viable yields. Hence, pressure can be used to increase the yield, as the reaction which produces methanol exhibits a decrease in volume, as disclosed in U.S. Pat. No. 3,326,956.

A low-pressure, copper-based methanol synthesis catalyst is commercially available from suppliers such as BASF, Johnson Matthey, and Haldor-Topsoe. Methanol yields from copper-based catalysts are generally over 99.5% of the converted $CO+CO_2$ present. Water is a by-product of the conversion of $CO_2$ to methanol and the conversion of CO synthesis gas to $C_2$ and $C_{2+}$ oxygenates. In the presence of an active water-gas shift catalyst, such as a methanol catalyst or a cobalt molybdenum catalyst the water equilibrates with the CO to give $CO_2$ and $H_2$. A paper entitled, "Selection of Technology for Large Methanol Plants," by Helge Holm-Larsen, presented at the 1994 World Methanol Conference, Nov. 30-Dec. 1, 1994, in Geneva, Switzerland, reviews the developments in methanol production and shows how further reduction in costs of methanol production will result in the construction of very large plants with capacities approaching 10,000 t per day.

Other processes for the production of $C_2$ and $C_{2+}$ alcohol(s), include the processes described hereinafter;

WO 8303409 describes a process whereby ethanol is produced by carbonylation of methanol by reaction with CO in the presence of a carbonylation catalyst to form ethanoic acid which is then converted to an ethanoate ester followed by hydrogenolysis of the ethanoate ester formed to give ethanol or a mixture of ethanol and another alcohol which can be separated by distillation. Carbonylation can be effected using a $CO/H_2$ mixture and hydrogenolysis can similarly be conducted in the presence of CO, leading to the possibility of circulating gas between the carbonylation and hydrogenolysis zones with synthesis gas, preferably a 2:1 $H_2$:CO molar mixture being used as make up gas.

U.S. Pat. No. 4,122,110 relates to a process for manufacturing alcohols, particularly linear saturated primary alcohols, by reacting CO with $H_2$ at a pressure between 2 and 25 MPa and a temperature between 150 and 400° C., in the presence of a catalyst, characterized in that the catalyst contains at least 4 essential elements: (a) copper (b) cobalt (c) at least one element M selected from chromium, iron, vanadium and manganese, and (d) at least one alkali metal.

U.S. Pat. No. 4,831,060 relates to the production of mixed alcohols from CO and $H_2$ gases using a catalyst, with optionally a co-catalyst, wherein the catalyst metals are molybdenum, tungsten or rhenium, and the co-catalyst metals are cobalt, nickel or iron. The catalyst is promoted with a Fischer-Tropsch promoter like an alkali or alkaline earth series metal or a smaller amount of thorium and is further treated by sulphiding. The composition of the mixed alcohols fraction can be selected by selecting the extent of intimate contact among the catalytic components.

Journal of Catalysis, 1988, 114, 90-99 discloses a mechanism of ethanol formation from synthesis gas over $CuO/ZnO/Al_2O_3$. The formation of ethanol from CO and $H_2$ over a CuO/ZnO methanol catalyst is studied in a fixed-bed microreactor by measuring the isotopic distribution of the carbon in the product ethanol when isotopically-enriched $^{13}C$ methanol was added to the feed.

SUMMARY OF THE INVENTION

As the importance of alcohols is ever increasing in today's world, so is the need and desire to produce alcohols with a higher carbon efficiency, a higher conversion and an improved selectivity from a carbonaceous feedstock. Hence, the present invention provides a process that allows one to produce alcohols from a carbonaceous feedstock, with improved carbon efficiency, a higher selectivity and in particular, with a more efficient conversion to ethanol.

BRIEF DESCRIPTION OF THE DRAWINGS

The invention is further described with reference to the accompanying drawings, in which.

Figure 1:
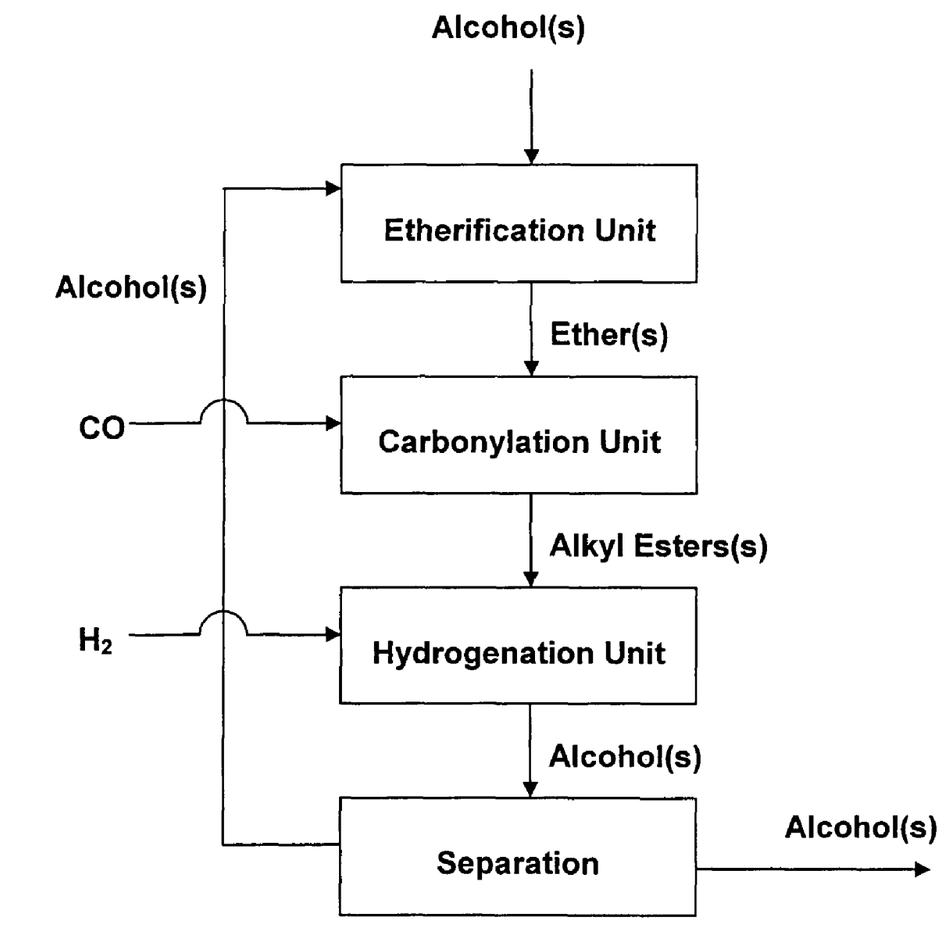
FIG. 1 represents an embodiment of a process scheme according to the present invention, wherein the references correspond to those used in the present description and appending claims.

For the purpose of the present invention and appending claims, the term 'homologation' is used to describe the process whereby one alcohol with n carbon atoms (e.g. methanol) enters the overall process and an alcohol containing n+1 carbon atoms (e.g. ethanol) exits the overall process.

For the purposes of the present invention and appending claims "alkyl esters" are a class of chemical compounds and functional groups and consist of a carboxylic acid in which at least one —OH (hydroxy) group is replaced by an —O-alkyl (alkoxy) group; the alkyl esters produced according to the present invention are preferably methyl ethanoate, ethyl ethanoate, methyl propanoate, ethyl propanoate, propyl butanoate and/or butyl pentanoate.

Thus, the present invention relates to a process for homologation of alcohol(s), characterised by the following steps:
1. introducing alcohol(s) into an etherification unit to produce alkyl ether(s),
2. introducing at least a part of the alkyl ether(s) from step 1, together with CO and optionally $H_2$, into a carbonylation unit, in the presence of an acidic homogeneous or heterogeneous carbonylation catalyst, to produce alkyl ester(s),
3. introducing at least a part of the alkyl ester(s) from step 2, together with $H_2$, into a hydrogenation unit, to produce homologated alcohol(s),
4. optionally recycling at least a part of the homologated alcohol(s) from step 3, into the etherification unit of step 1, and
5. recovering the targeted alcohol(s) from the hydrogenation unit of step 3.

Wherein the alcohol(s) introduced into the etherification unit (i.e. in step 1) may be produced by any appropriate method known to those skilled in the art, e.g. via fermentation (described hereinabove).

For the purposes of the present invention and appending claims the following terms are defined hereinafter:
The 'dew point temperature' is a threshold temperature, for example, for a given pure component or mixture of components, at a given pressure, if the system temperature is raised to above the dew point temperature, the mixture will exist as a dry gas. Likewise below the dew point temperature, the mixture will exist as a vapour containing some liquid.
'Gas' and/or 'gas phase' are defined as a pure component, or mixture of components, that are above the dew point temperature.
'Gas hourly space velocity' (GHSV) is defined as the volume of gas fed per unit volume of catalyst per hour, at standard temperature (0° C.) and pressure (0.101325 MPa).
'Liquid hourly space velocity' (LHSV) is defined as the volume of liquid fed per unit volume of catalyst per hour.

The invention described hereinabove has application for the homologation of existing petrochemical and biomass derived feedstocks, namely alcohols but also can also be used to homologate ethers and esters. The utility of the process can be further widened by including a further process step, for example carboxylic acids can be homologated by adding an esterification stage in order to convert them into a suitable ester intermediate. Similarly olefins can be homologated by this process by adding a hydration stage to generate an alcohol feedstock. In particular this invention finds application in the generation of improved fuels and petrochemical feedstocks. For example, the homologation of methanol by one pass through the described process can yield ethanol, a valuable gasoline blending feedstock. Additionally, a further pass (recycle of methanol and some ethanol) through the process described hereinabove can generate n-propanol, a material with superior gasoline blending properties (e.g. calorific value and vapour pressure). The passing of n-propanol through the process described hereinabove yields butanol(s) which have desirable properties as gasoline blending components and as intermediates in chemicals and fuels e.g. di-n-butyl ether has a high cetane blending value. The starting alcohol, as described need not be solely methanol but can include other alcohols and mixtures such as bioethanol or other bioalcohols (e.g. methanol, ethanol, propanol and butanol). The use of bioalcohols in this process is advantageous as homologation will improve in general the blending properties of the alcohols in fuels and thereby improve the blended fuel properties and thus allow incorporation of higher levels of renewable feedstocks than otherwise possible. This is advantageous in an environment where reduced greenhouse emissions and improved sustainability are important goals. This process also can directly yield valuable derivatives of alcohols such as di-butyl ether, ethyl-pentyl ether which could find application as a diesel blending component, and valuable chemicals such as propyl propanoate and ethyl ethanoate (valuable solvents) and isobutanol a precursor for isobutene.

The alcohol feedstocks can be obtained from synthesis gas by methods previously described in this document hereinabove. These feedstocks also can be obtained by hydration of olefins in which case the higher olefins yield secondary and tertiary alcohols e.g. propene yields predominately isopropanol and isobutene will yield t-butanol. Typical sources of such olefin streams include the catalytic cracking of hydrocarbons as is commonly practiced on petroleum refineries sites, the methanol-to olefin (MTO) and oxygenate-to-olefin (OTO) processes, and dismutation reactions. Thus by including a hydration stage or an alcohol addition stage (in which case an ether feedstock is obtained) these by-product streams can be usefully employed.

The process is particularly advantageous for these feedstocks as it produces, for $C_3$ and higher olefins, desirable branched primary alcohol products not obtainable by direct hydration of the corresponding olefin. For example propene can be converted to isobutanol and tertiary butanol (2,methylpropan-2-ol) to 2,2,dimethyl propan-1-ol.

The present invention also relates to a process for the conversion of a carbonaceous feedstock into alcohol(s), wherein the carbonaceous feedstock is first converted into synthesis gas; which is subsequently converted into homologated alcohol(s), characterised by the following steps:
1. introducing a carbonaceous feedstock, into a synthesis gas generation unit, in order to produce a mixture of carbon oxide(s) and $H_2$ (synthesis gas),
2. introducing at least a part of the carbon oxide(s) and $H_2$, from step 1, into an alcohol synthesis unit, to produce alcohol(s),
3. introducing at least a part of the alcohol(s) from step 2, into an etherification unit to produce alkyl ether(s),
4. introducing at least a part of the alkyl ether(s) from step 3, together with CO and optionally $H_2$, into a carbonylation unit, in the presence of an acidic homogeneous or heterogeneous carbonylation catalyst, to produce alkyl ester(s),
5. introducing at least a part of the alkyl ester(s) from step 4, together with $H_2$, into a hydrogenation unit, to produce homologated alcohol(s),
6. optionally recycling at least part of the homologated alcohol(s) from step 5, into the etherification unit of step 3, and
7. recovering the targeted alcohol(s) from the hydrogenation unit of step 5.

According to one aspect of the present invention, the synthesis gas feedstock, a mixture of carbon oxide(s) and $H_2$, that is used to produce the methanol feed stream, is preferably produced from a carbonaceous feedstock.

The carbonaceous feedstock is preferably a material such as biomass, plastic, naphtha, refinery bottoms, crude synthesis gas (from underground coal gasification or biomass gasification), smelter off gas, municipal waste, coal bed methane, coal, and/or natural gas, with coal and natural gas being the preferred sources. To one skilled in the art a combination of sources can also be used, for example coal and natural gas to advantageously increase the $H_2$ to carbon ratio.

Natural gas commonly contains a range of hydrocarbons (e.g. $C_1$-$C_3$ alkanes), in which methane predominates. In addition to this, natural gas will usually contain nitrogen, $CO_2$ and sulphur compounds. Preferably the nitrogen content of the feedstock is less than 40 mol %, more preferably less than 10 mol % and most preferably less than 2 mol %.

Processes for producing synthesis gas, in a synthesis gas plant, are well known. Each method has its advantages and disadvantages, and the choice of using a particular reforming process over another is governed by economic and available feed stream considerations, as well as by the desire to obtain the optimum $(H_2-CO_2):(CO+CO_2)$ molar ratio in the resulting synthesis gas that is suitable for further chemical processing. A discussion of the available synthesis gas production technologies is provided in both Hydrocarbon Processing, 1999, 78:4, 87-90, and 92-93 and Petrole et Techniques, 1998, 415, 86-93, and are both hereby incorporated by reference.

It is also known that the synthesis gas may be obtained by catalytic partial oxidation of hydrocarbonaceous material in a microstructured reactor as exemplified in IMRET 3: Proceedings of the Third International Conference on Microreaction Technology, ed. W. Ehrfeld, Springer Verlag, 1999, pages 187-196. Alternatively, the synthesis gas may be obtained by short contact time catalytic partial oxidation of hydrocarbonaceous feedstocks as described in EP 0303438. The synthesis gas can also be obtained via a 'compact reformer' process as described in Hydrocarbon Engineering, 2000, 5:5, 67-69; Hydrocarbon Processing, 2000, 79:9, 34; Today's Refinery, 2000, 15:8, 9; WO 9902254; and WO 0023689.

Typically, for commercial synthesis gas production the pressure at which the synthesis gas is produced from a steam reformer ranges from approximately 0.1 to 10 MPa, preferably 2 to 3 MPa and the temperatures at which the synthesis gas exits the reformer ranges from approximately 700 to 1000° C. Likewise, for commercial synthesis gas production the pressure at which the synthesis gas is produced from an auto-thermal reformer ranges from approximately 0.1 to 10 MPa, preferably 2 to 5 MPa and the temperatures at which the synthesis gas exits the reformer ranges from approximately 700 to 1300° C. Where the high temperatures are necessary in order to produce a favourable equilibrium for synthesis gas production, and to avoid metallurgy problems associated with carbon dusting. The synthesis gas contains a molar ratio of $(H_2-CO_2):(CO+CO_2)$ ranging from 0.8 to 3.0, which is dependent on the carbonaceous feedstock(s) and the method of reforming used. For example, when natural gas is used as the carbonaceous feedstock for steam reforming, the synthesis gas obtained usually has a maximum $(H_2-CO_2):(CO+CO_2)$ ratio of 3.0. However, when natural gas is used as the carbonaceous feedstock for autothermal reforming, the synthesis gas obtained usually has a $(H_2-CO_2):(CO+CO_2)$ ratio of 1.5.

According to a preferred embodiment of the present invention, the molar ratio, $(H_2-CO_2):(CO+CO_2)$, of the synthesis gas stream exiting the synthesis gas generation unit(s) is greater than 1.6, more preferably greater than 1.8 and most preferably greater than 2.0. Preferably, the molar ratio, $(H_2-CO_2):(CO+CO_2)$, of said synthesis gas stream exiting the synthesis gas generation unit(s) is less than 3.0, preferably less than 2.75, more preferably less than 2.4 and most preferably less than 2.2.

Whilst the objective of the present invention is to homologate alcohols to produce higher alcohols, it is obvious for the man skilled in the art that the present invention may also allow to target further products, such as alkyl ethers and/or alkyl esters and/or carboxylic acids, together with said alcohols, wherein these said further products are present as intermediates and/or precursors in the process of the present invention. When ester and/or acid products are targeted then the $(H_2-CO_2):(CO+CO_2)$ of the synthesis gas required is preferably lower than the aforementioned values.

According to another embodiment of this invention when the carbonaceous feedstock used for synthesis gas generation is not an aliphatic hydrocarbon (e.g. coal, aromatic material, biomass) the molar ratio $(H_2-CO_2):(CO+CO_2)$ of the exit synthesis gas is preferably adjusted to the target value by addition of $H_2$ or removal of $CO_2$.

$CO_2$ may be removed by the use of a simple, yet effective, separation method known to those skilled in the art, for example, a "membrane separation method". Such membrane technologies can be found in 'Purification and Recovery Options for Gasification' D. J. Kubek, E. Polla, F. P. Wilcher, UOP, 1996.

Alternatively, $CO_2$ may be recovered and removed by any suitable method(s) known to those skilled in the art, for example, by reacting with amines; performing a methanol wash (i.e. the RECTISOL process) and/or by using hot potassium carbonate (e.g. the BENFIELD process).

According to a preferred embodiment of the present invention, the exit stream obtained from the synthesis gas reactor (e.g. using a steam reformer), comprises essentially a mixture of carbon oxide(s) and $H_2$. It can also comprise water, nitrogen and traces of unconverted hydrocarbons (e.g. $C_1$-$C_3$ alkanes).

According to a preferred embodiment of the present invention, during synthesis gas generation, an additional stage may be employed whereby the feedstock is first purified to remove sulphur and other potential catalyst poisons (such as halides or metals e.g. mercury) prior to being converted into synthesis gas; alternatively this treatment can also be performed after synthesis gas preparation for example, when coal or biomass are used.

According to an embodiment of the present invention, at least part of the said synthesis gas stream is then introduced into an alcohol synthesis unit, in order to produce a stream comprising alcohols(s). Preferably the molar ratio, $(H_2-CO_2):(CO+CO_2)$, of said synthesis gas feed stream fed into the alcohol synthesis unit is greater than 1.6, more preferably greater than 1.8 and most preferably greater than 2.0. Preferably the molar ratio, $(H_2-CO_2):(CO+CO_2)$, of said synthesis gas feed stream fed into the alcohol synthesis unit is less than 3.0, more preferably less than 2.5 and most preferably less than 2.2.

According to a preferred embodiment of the present invention, the alcohol synthesis unit may be any reactor that is suitable for producing alcohol, for example a fixed bed reactor, which can be run with or without external heat exchange equipments e.g. a multi-tubular reactor; or a fluidised bed reactor; or a void reactor.

When the alcohol synthesis unit is used to produce methanol it is preferably operated at a temperature of greater than 200° C., more preferably greater than 220° C. and most preferably greater than 240° C.; and preferably less than 310° C., more preferably less than 300° C. and most preferably less than 290° C. Likewise, it is operated at pressure of preferably greater than 2 MPa and most preferably greater than 5 MPa; and preferably less than 10 MPa and most preferably less than 9 MPa. In fact, since methanol synthesis is an exothermic reaction, the chosen temperature of operation is governed by a balance of promoting the forward reaction (i.e. by not adversely affecting the equilibrium) and aiding the rate of conversion (i.e. higher productivity).

The catalysts used for methanol synthesis in particular can be divided into two groups:
  i. the high pressure zinc catalysts, composed of zinc oxide and a promoter; and
  ii. low pressure copper catalysts, composed of zinc oxide, copper oxide, and a promoter.

Hence, according to a preferred embodiment of the present invention, a preferred methanol synthesis catalyst is a mixture of copper, zinc oxide, and a promoter such as, chromia or alumina. Under the aforementioned operating conditions, these said mixtures can catalyse the production of methanol from CO and $H_2$ with a high selectivity.

When, the alcohol synthesis unit is used to produce a mixture of alcohols, such as methanol, ethanol, propanol(s) (n-propanol with low amounts of iso-propanol), and butanol(s) (n-butanol and iso-butanol), the operating conditions of the alcohols synthesis unit may vary depending on the catalyst employed. Suitable catalysts include modified methanol synthesis catalysts, modified Fischer-Tropsch catalysts, metal mixed oxide catalysts, rhodium based catalysts and molybdenum sulphide based catalysts.

Molybdenum sulphide based catalysts are preferred; these can be modified by a promoter. Promoter(s) can be added as salts during the catalyst preparation; the preferred promoter(s) are potassium ions and are derived from a salt of potassium, such as potassium carbonate or ethanoate. The preferred loadings of potassium ions per molybdenum is comprised between 0.7 and 1.5, most preferably between 1.0 and 1.4.

The preferred catalyst for alcohol synthesis, according to the present invention, is a molybdenum sulphide based catalysts containing cobalt, the cobalt to molybdenum molar ratio being preferably comprised between 0.5 and 3.0, more preferably between 0.5 and 1.0 and most preferably between 0.5 to 0.9.

When molybdenum sulphide based catalysts are employed the alcohol synthesis unit is preferably operated at a temperature of greater than 150° C., preferably greater than 250° C. and most preferably greater than 280° C.; and less than 400° C., preferably less than 350° C. and most preferably less than 320° C. Likewise, it is operated at pressure of greater than 2 MPa and preferably greater than 8 MPa; and less than 20 MPa and preferably less than 15 MPa. According to a preferred embodiment of this aspect of the present invention, the stream exiting the alcohol synthesis unit is subsequently purified, by any method known to those in the art, to remove any by-products such as alkanes, aldehydes, ketones and/or water.

According to the present invention, the alcohols produced in the alcohol synthesis unit are then introduced into an etherification unit to produce alkyl ether(s). For example, dimethyl ether is commonly produced by the Lewis or Bronsted acid catalysed etherification of methanol; numerous catalysts for this reaction have been reported e.g Houben-Weyl, vol. VI/3, part 3, Georg Thieme Verlag, Stuttgart 1965, pp. 17, 18. Dr. Alexander Wacker, Gesellschaft für elektrochemische Industrie GmbH, DE 680328, 1934 (P. Halbig, O. Moldenhauer). R. L. Brown, W. W. Odells, U.S. Pat. No. 1,873,537, 1927. N. V. de Bataafsche Petroleum Maatschappij, FR 701335, 1930; GB 332756, 1929; GB 350010, 1931; GB 403402, 1932. Further examples of etherification catalysts include: iron chloride; copper sulphate; copper chloride; manganese chloride; aluminium chloride; aluminium sulphate; chromium sulphate; alums; thorium compounds; aluminium oxide; titanium oxide; barium oxide; silica gel; aluminium phosphate; and acidic ionic liquids. The chosen etherification catalyst may be either homogeneous or heterogeneous.

According to the present invention the preferred etherification catalysts are heterogeneous catalysts, such as aluminium oxides and aluminium silicate, which can be modified by doping. Corresponding etherification catalysts and process operating conditions that may be advantageously used according to the present invention are described in Mobil Oil Corporation, DE 2818831, 1978 (F. G. Dwyer, A. B. Schwartz); DE-OS 3201155, 1982 (W. K. Bell, C. Chang); Du Pont, EP-A 99676, 1983 (D. L. Brake); Mitsubishi Chemical Industries, EP-A 124078, 1984 (N. Murai, K. Nakamichi, M. Otake, T. Ushikubo).

Zeolites, strong acid ion exchange resins, supported heteropolyacids (such as silicotungstenic acid) and mixtures thereof, can also advantageously be used as etherification catalysts; and supported heteropolyacids catalysts are preferably used according to the present invention.

During the alcohol etherification process to produce alkyl ether(s), e.g. methanol to dimethyl ether (DME) and/or methanol and ethanol to dimethyl ether and methylethyl ether and diethyl ether, water is also produced. It is preferred according to the present invention to proceed with the removal of said water prior to the introduction of the alkyl ether(s) to the next stage of this invention. Other ethers can also be produced during the etherification process depending on the composition of the alcohol feedstock introduced into the etherification unit, e.g. dipropyl ether, dibutyl ether, dipentyl ether and ethylpentyl ether can also be produced and some of the said ethers can advantageously be separated, isolated and used as diesel additives.

According to the present invention, at least a part of the aforementioned alkyl ether(s) together with CO and optionally $H_2$, are introduced into a carbonylation unit in the presence of an acidic homogeneous or heterogeneous carbonylation catalyst. The applicants have found a preferred embodiment, whereby it is especially advantageous (e.g. increased catalyst lifetime) to conduct the carbonylation process in the presence of $H_2$. Preferably at least part, most preferably all, of the said alkyl ether(s), emanate from the aforementioned etherification unit. However, according to an alternative embodiment of the present invention, at least a part of the alkyl ether introduced into the carbonylation unit may also originate from a direct synthesis gas to alkyl ether process (e.g. synthesis gas to dimethyl ether). For example, the reaction to produce dimethyl ether is exothermic and equilibrium controlled, as is the methanol synthesis reaction; however the reaction to produce dimethyl ether is more thermodynamically favourable than the methanol synthesis, under methanol synthesis reaction conditions. This has lead to close-coupling of these reactions in a single reactor as a means of increasing the potential yield per pass. This can be achieved by either adding acidity to a methanol synthesis catalyst, or by mixing an acidic catalyst with a methanol synthesis catalyst. Such processes are often referred to as direct synthesis e.g. Snamprogetti, SpA., DE 2 362944, 1973 (G. Giorgio); DE 2757788, 1977 (G. Manara, B. Notari, V. Fattore); DE 3220547, 1982 (G. Manara). The same coupling can also be applied to mixed alcohol synthesis, for example the inclusion of a post acid bed in a mixed alcohol synthesis unit can be used to produce alkyl ether(s).

Suitable carbonylation catalysts used in the present invention are acidic homogeneous or acidic heterogeneous catalysts. For example, the catalyst can be selected from homogeneous strong acid catalysts, e.g. phosphoric acid; and, heterogeneous analogues such as supported phosphoric acid and SAPO's catalysts. Other heterogeneous catalysts include zeolites; strong acid ionic resins catalysts; and mixtures thereof.

According to an embodiment of the present invention the carbonylation process for producing a product comprising a alkyl ester(s) of a lower aliphatic carboxylic acid comprises reacting a alkyl ether(s) with carbon monoxide under substantially anhydrous conditions in the presence of hydrogen and of a catalyst comprising a zeolite having at least one 8-member ring channel, said 8-member ring channel being interconnected with a channel defined by a ring with greater than or equal to 8 members, said 8-member ring having a window size of at least 2.5 Angstroms×at least 16 Angstroms and at least one Brønsted acid site and wherein the zeolite has a silica:$X_2O_3$ ratio of at least 5, wherein X is selected from aluminium, boron, iron, gallium and mixtures thereof, such as mordenite or ferrierite.

One component of the feed to the carbonylation process comprises (primarily) alkyl ether(s), which according to the present invention are produced during the aforementioned etherification process. Said alkyl ether(s) are compounds having the formula in which $R_1$ and $R_2$ are independently $C_1$-$C_6$ alkyl groups. The total number of carbon atoms in groups $R_1$ and $R_2$, if $R_1$ and $R_2$ are alkyl groups, is from 2 to 12, preferably from 2 to 8, most preferably from 2 to 6. Preferably, $R_1$ and $R_2$ are straight-chain alkyl groups, most preferably straight-chain alkyl groups having from 1 to 3 carbon atoms each.

The carbonylation reaction overall can be depicted as

The term "alkyl" as used herein means a straight or branched chain, saturated aliphatic group, or a combination thereof, that has the number of carbon atoms designated (i.e. $C_3$ means three carbon atoms). Examples of acyclic alkyl groups include groups such as methyl, ethyl, n-propyl, isopropyl, n-butyl, t-butyl, isobutyl, sec-butyl, and the various pentyl and hexyl isomers.

The term "alkylene" as used herein refers to saturated aliphatic moieties that may form two single bonds with other moieties. This group includes, for example, methylene (—$CH_2$—), ethylene (—$CH_2CH_2$—) and hexylene [(—$CH_2$—)$_6$]. Whilst alkylene groups may be straight or branched chain groups, straight-chain alkylene groups are preferred for use in the carbonylation process of this invention.

If the alkyl ether is a symmetrical ether, e.g. dimethyl ether, the main product will be the corresponding alkyl ester of an aliphatic acid (in this case, methyl ethanoate). If the ether is asymmetrical, the product will comprise one or both of the two possible carboxylic acid esters, depending on which of the two C—O bonds is cleaved in the reaction. For example, if the feed is methyl ethyl ether ($R_1$=methyl; $R_2$=ethyl), then the product will comprise ethyl ethanoate and/or methyl propanoate.

The feed to the carbonylation unit may comprise substantially pure carbon monoxide (CO), for example, carbon monoxide typically provided by suppliers of industrial gases, or it may contain impurities that do not interfere with the conversion of the alkyl ether to the desired ester, such as nitrogen, helium, argon, methane and/or carbon dioxide. For example, the feed may comprise CO that is typically made commercially by removing hydrogen from the synthesis gas (produced during the aforementioned synthesis gas generation stage), via a cryogenic separation and/or use of a membrane.

In fact, according to a preferred embodiment of the present invention, the carbon monoxide feed to the carbonylation unit contains substantial amounts of hydrogen. For example, the feed introduced in the carbonylation unit may be what is commonly known as synthesis gas, and is preferably derived from the aforementioned synthesis gas generation unit.

As indicated, the carbonylation process takes place in the presence of both carbon monoxide and hydrogen; preferably, the ratio of carbon monoxide: hydrogen is in the range 1:3 to 15:1 on a molar basis, such as 1:1 to 10:1.

Zeolites, both natural and synthetic are microporous crystalline aluminosilicate materials having a definite crystalline structure as determined by X-ray diffraction. The chemical composition of zeolites can vary widely but they typically consist of $SiO_2$ in which some of the Si atoms may be replaced by tetravalent atoms such as Ti or Ge, by trivalent atoms such as Al, B, Ga, Fe or by bivalent atoms such as Be, or by a combination thereof. A zeolite is comprised of a system of channels which may be interconnected with other channel systems or cavities such as side-pockets or cages. The channel systems are uniform in size within a specific zeolite and may be three-dimensional but are not necessarily so and may be two-dimensional or one-dimensional. The channel systems of a zeolite are typically accessed via 12-member rings, 10-member rings or 8 member rings. The specific zeolite mentioned hereinabove contains at least one channel which is defined by an 8-member ring. Preferred zeolites are those which do not have side-pockets or cages within the zeolite structure. The *Atlas of Zeolite Framework Types* (C. Baerlocher, W. M. Meier, D. H. Olson, 5$^{th}$ ed. Elsevier, Amsterdam, 2001) in conjunction with the web-based version (http://www.iza-structure.org/databases/) is a compendium of topological and structural details about zeolite frameworks, including the types of ring structures present in the zeolite and the dimensions of the channels defined by each ring type. For the purposes of the present invention, the term 'zeolite' also includes materials having a zeolite-type structure such as delaminated porous crystalline oxide materials such as ITQ-6 and pillared layered oxide materials such as ITQ-36.

The carbonylation process of the present invention preferably employs a zeolite having at least one channel defined by an 8-member ring of tetrahedrally co-ordinated atoms (tetrahedra) with a window size having a minimum dimension of 2.5 Angstroms×3.6 Angstroms. The 8-member ring channel is interconnected with at least one channel defined by a ring with equal to or greater than 8 members, such as 10 and/or 12 members. The interconnected 8-, 10, and 12-member ring channels provide access to Brønsted acid sites contained in the 8-member ring channels to enable the carbonylation of the alkyl ether(s), such as dimethyl ether to proceed at acceptable rates.

The zeolite for use in the carbonylation process of the present invention may consist of interconnected channels defined solely by 8-member rings, such as zeolites of framework type CHA, for example, chabazite and framework type ITE, for example ITQ-3. Preferably, however, the zeolite has at least one channel formed by an 8-member ring and at least one interconnecting channel defined by a ring with greater than 8 members, such as a 10, and/or 12 member ring. Non-limiting examples of zeolites having 8-member ring channels and interconnecting larger ring channel systems include zeolites of framework type MOR, for example, mordenite, FER, such as ferrierite and ITQ6, OFF, for example, offretite, GME, for example Gmelinite, MFS, such as ZSM-57, EON such as ECR-1 and ETR such as ECR-34. Preferably, the zeolites for use in the process of the present invention have at least one 8-member ring channel interconnected with at least one 12-member ring channel, such as those of framework type MOR, OFF and GME, for example, mordenite, offretite and gmelinite.

The aperture (pore width) of an 8-member ring channel of the zeolite has a minimum dimension of 2.5×3.6 Angstroms. Channel dimensions of zeolite framework types may be found, for example, in the *Atlas of Zeolite Framework Types*. In addition, M. D. Foster, I. Rivin, M. M. J. Treacy and O. Delgado Friedrichs in "A geometric solution to the largest-free-sphere problem in zeolite frameworks" Microporous and Mesoporous Materials 90 (2006) 32-38, have used Delaunay triangulation methods applied to known zeolite frameworks and have tabulated the largest free-sphere diameters for diffusion along the three principal crystallographic directions for the 165 zeolite frameworks that are currently listed in the *Atlas of Zeolite Framework Types*. Ring window sizes may be modified by suitable atomic substitutions that change bond lengths and bond angles of the tetrahedrally co-ordinated atoms and the bridging oxygens.

A partial listing of zeolite framework types having at least one interconnected 8 member ring channel of minimum dimension of 2.5×3.6 Angstroms taken from *The Atlas of Zeolite Framework Types* is given below:

| MOR | Mordenite | 12 (6.5 × 7.0 Å) | 8 (3.4 × 4.8 Å) | 8 (2.6 × 5.7 Å) |
|---|---|---|---|---|
| OFF | Offretite | 12 (6.7 × 6.8 Å) | 8 (3.6 × 4.9 Å) | |
| FER | Ferrierite | 10 (4.2 × 5.4 Å) | 8 (3.5 × 4.8 Å) | |
| CHA | Chabazite | 8 (3.8 × 3.8 Å) | | |
| ITE | ITQ3 | 8 (3.8 × 4.3 Å) | 8 (2.7 × 5.8 Å) | |
| GME | Gmelinite | 12 (7.0 × 7.0 Å) | 8 (3.6 × 3.9 Å) | |
| ETR | ECR-34 | 18 (10.1 Å) | 8 (2.5 × 6.0 Å) | |
| MFS | ZSM-57 | 10 (5.1 × 5.4 Å) | 8 (3.3 × 4.8 Å) | |
| EON | ECR-1 | 12 (6.7 × 6.8 Å) | 8 (3.4 × 4.9 Å) | 8 (2.9 × 2.9 Å) |

Zeolites are available from commercial sources. Alternatively they may be synthesized using known techniques. In general, synthetic zeolites are prepared from aqueous reaction mixtures comprising sources of appropriate oxides. Organic directing agents may also be included in the reaction mixture for the purpose of influencing the production of a zeolite having the desired structure. After the components of the reaction mixture are properly mixed with one another, the reaction mixture is subjected to appropriate crystallization conditions. After crystallization of the reaction mixture is complete, the crystalline product may be recovered from the remainder of the reaction mixture. Such recovery may involve filtering the crystals, washing with water followed by a calcination treatment at high temperature. The synthesis of zeolites is described in numerous references. For example, zeolite Y and its synthesis is described in U.S. Pat. No. 3,130,007, zeolite ZSM-23 is described in U.S. Pat. No. 4,076,842 and J. Phys. Chem. B, 109, 652-661 (2005), Zones, S. I. Darton, R. J., Morris, R and Hwany, S-J; ECR-18 is described in Microporous Mesoporous Mat., 28, 233-239 (1999), Vaughan D. E. W. & Strohmaier, K. G.; Theta-1 is described in Nature, 312, 533-534 (1984). Bath, S. A. I., Smith W. G., White, D. and Young, D.; Mazzite is described in Microporous Mesoporous Mat., 63, 33-42 (2003), Martucci, A, Alberti, A, Guzmar-Castillo, M. D., Di Renzo, F. and Fajula, F.; Zeolite L is described in Microporous Mesoporous Mat., 76; 81-99 (2004), Bhat, S. D., Niphadkair, P. S., Gaydharker, T. R., Awate, S. V., Belhekar, A. A. and Joshi, P. N and also in J. Ind. Eng. Chem. Vol. 10, No. 4 (2004), 636-644, Ko Y. S, Aim W. S and offretite is described in Zeolites 255-264, Vol. 7, 1987 Howden M. G.

The zeolite catalyst for use in the carbonylation process of the present invention is used in the acid form, generally referred to as the 'H' form of the zeolite, for example, H-mordenite, H-ferrierite. Other forms of the zeolite, such as the $NH_4$ form can be converted to the H-form, for example, by calcining the $NH_4$ form at elevated temperature. The acid form of a zeolite will possess Brønsted acid ($H^+$) sites which are distributed among the various channel systems in the zeolite. For example, H-mordenite has $H^+$ sites located in the 12 member ring channels and in the 8 member ring channels. The number or concentration of $H^+$ species residing in any particular channel system can be determined by known techniques such as infra-red and NMR spectroscopic techniques. Quantification of Brønsted acidity by FTIR and NMR spectroscopy is described, for example, in Makarova, M. A., Wilson, A. E., van Liemt, B. J., Mesters, C. de Winter, A. W., Williams, C. Journal of Catalysis 1997, 172, (1), 170. The two types of channels in H-Mordenite (defined by 12 member rings and 8 member rings) give rise to at least two bands associated with the hydroxyl region of H-mordenite, one corresponding to vibration into the larger pores and the other, at a lower frequency, vibrating into the smaller pores. It has been shown that there is a correlation between the number of $H^+$ sites located in an 8-member ring channel and the carbonylation rate whereas no such correlation has been observed for 12-member ring channels. It has been found that carbonylation rates increase in parallel with the number of $H^+$ sites within 8 member ring channels. In contrast, no correlation is evident with the number of $H^+$ sites within 12 member ring channels. The number of $H^+$ sites within 8-member ring channels can be controlled by replacement of the $H^+$ with metal cations such as $Na^+$ or $Co^{2+}$ using known ion-exchange techniques.

The chemical composition of a zeolite (that may be used to catalyse the carbonylation process) may be expressed as involving the molar relationship:

$$SiO_2 : X_2O_3$$

wherein X is a trivalent element, such as aluminium, boron, iron and/or gallium, preferably aluminium. The $SiO_2:X_2O_3$ ratio of a given zeolite is often variable. For example, it is known that mordenite can be synthesized with $SiO_2: Al_2O_3$ ratios of 6 to 90 or greater, zeolite Y, from about 1 to about 6, chabazite from about 2 to 2000 and gmelinite may be synthesised with $SiO_2: Al_2O_3$ ratios of greater than 4. In general, the upper limit of the $SiO_2:X_2O_3$ ratio is unbounded, for example, the zeolite ZSM-5. The specific zeolite mentioned hereinabove have a $SiO_2:X_2O_3$ molar ratio of at least 5, preferably in the range 7 to 40, such as 10 to 30. Suitably, the $SiO_2:X_2O_3$ molar ratio is less than or equal to 100. Particular $SiO_2:X_2O_3$ ratios can be obtained for many zeolites by dealumination (where X is Al), by standard techniques using high temperature steam treatment or acid washing.

In one embodiment, the catalyst used in the carbonylation unit is composed of mordenite or ferrierite, or mixtures or combinations of the two, either per se (i.e., in the acid form, generally referred to as H-mordenite and H-ferrierite), or optionally ion-exchanged or loaded with one or more metals such as copper, nickel, iridium, rhodium, platinum, palladium, or cobalt. Mordenite catalysts may, in addition to silicon and aluminum atoms, contain further elements in the zeolite framework, particularly gallium and/or iron. Ferrierite catalysts may, in addition to silicon and aluminum atoms, contain further elements in the zeolite framework, particularly boron, gallium and/or iron. Framework modifier elements to both types of catalysts may be introduced to the framework by any conventional means. Where a framework modifier element is used in either a mordenite or ferrierite catalyst, the catalyst suitably has a ratio of silica to the oxide of the framework modifier element would be from about 10:1 to about 100:1. T-atom incorporation where T is B, Ga or Fe into zeolites of the ferrierite structure is disclosed in Melian-Cabrera et al., *Catalysis Today* 110 (2005) 255-263; Shawki et al., EP (Application) 234,766 (1987), Sulikowski et al., *J. Chem. Soc., Chem. Comm.*, 1289 (1989); Borade et al., *J. Chem. Soc., Chem. Comm.*, 2267 (1996); Jacob et al., *Zeolites* 430 (1993) Vol. 13. T-atom incorporation into zeolites of the mordenite structure where the T-atom is Ga or Fe is disclosed in Smith, WO 05/085162.

Mordenite (commonly available as Na-mordenite, $NH_4$-mordenite or H-mordenite) is a member of the aluminosilicate zeolite class of minerals. The formula of mordenite in its Na-form is usually given as $Na(AlSi_5O_{12}).3H_2O$ or $(Na_2,Ca,K_2)Al_2Si_{10}O_{24}.7H_2O$. It is available from a number of commercial sources of such materials. H-Mordenite has elliptical 6.5×7.0 Å channels (12 member rings with window openings running in the crystallographical c-direction). It also has a system of smaller channels running perpendicular to the 12 member ring channels (and running in the b-direction). These small channels consist of 3.4×4.8 Å channels having 8 member ring windows of these dimensions. The mordenite structure also possesses a zig-zag Y-branching of the pore structure due to twisted 8 member rings (in the crystallographic c-direction) This results in a distorted window to each side of the Y-branching of 2.6×5.7 Å. Ferrierite is another member of the aluminosilicate zeolite class of minerals, also available in the Na—, $NH_4$— and H— forms. In the Na-form its formula generally is given as $Na_{0.8}K_{0.2}MgSi_{15}Al_3O_{36}.9H_2O$ or $(Mg,Na_2,K_2,Ca)_{3-5}Mg[Al_{5-7}Si_{27.5-31}O_{72}].18H_2O$. It, too, is available from various commercial sources. Additional information on these and other materials can be found on the website of the International Zeolite Association, www.iza-online.org. H-Ferrierite has 4.2×5.4 10-member ring channels running in the crystallographic c-direction and 3.5×4.8 8-member ring channels running in the b-direction.

The carbonylation reaction is to be conducted substantially in the absence of water when using the specific zeolite mentioned hereinabove, for example by drying the zeolite catalyst before beginning the operation, for example, by preheating to 400-500° C.

In general, when a zeolite catalyst is employed, the carbonylation process is run at temperatures at or below about 600° C., that is, at temperatures of from about 150 to about 600° C., preferably from about 250 to about 400° C. One feature of the process is that, surprisingly, the carbonylation of dimethyl ether (DME) to methyl ethanoate using mordenite zeolite based catalysts and in the substantial absence of water can be performed with very high selectivities.

Typical total operating pressures when zeolites are employed in the carbonylation process are from 1 MPa to about 20 MPa, preferably from about 1 MPa to about 15 MPa and most preferably from about 2.5 MPa to about 10 MPa; preferably with carbon monoxide pressures greater than 1 MPa and dimethyl ether pressures below 0.5 MPa.

The zeolite carbonylation process is carried out under substantially anhydrous conditions, i.e. in the substantial absence of water. The carbonylation of dimethyl ether to methyl ethanoate does not generate water in-situ. Water has been found to inhibit the carbonylation of dimethyl ether to form methyl ethanoate. This is in comparison to prior art processes, in which dimethyl ether was a co-feed, and in which water was also fed to the reaction. Water is thus kept as low as feasible, in order to allow the desired reaction to proceed best. To accomplish this, the alkyl ether and carbon monoxide reactants and the catalyst are preferably dried prior to introduction into the process.

The carbonylation process may be run as either a continuous or a batch process, with continuous processes typically preferred. Essentially, the heterogeneous process is a gas-phase operation, with reactants being introduced in either liquid or gaseous phase, and products withdrawn as gases. As desired, the reaction products may subsequently be cooled and condensed. The heterogeneous catalyst may be used as convenient, in either a fixed bed or a fluidized bed. In operating the process, unreacted starting materials may be recovered and recycled to the unit. The product alkyl esters are then fed to the hydrogenation unit; however, some alkyl esters (e.g. methyl ethanoate) may also be recovered and sold as such, or may be forwarded to other chemical process units as desired. Preferably, the entire reaction product may be sent to the hydrogenation unit for conversion of the alkyl esters into the corresponding esters.

The alkyl ester product may be removed from the carbonylation unit by withdrawing liquid reaction composition and separating the alkyl ester product by one or more flash and/or fractional distillation stages from the other components. The alkyl ester product may also be removed as a vapour from the stream exiting the carbonylation unit. According to a preferred embodiment of the present invention, during the above separation stage, water is selectively removed from the carbonylation process in order to maintain the aforementioned operating conditions.

According to a preferred embodiment of the present invention, the separated alkyl ester(s) from the stream exiting the carbonylation unit are then purified to remove carboxylic acids (e.g. ethanoic acid) and water, before being introduced into the hydrogenation unit.

After purification and before introduction into the hydrogenation unit, the alkyl ester stream contains preferably less than 5 wt % of carboxylic acids, more preferably less than 1 wt %, even more preferably less than 0.1 wt % and most preferably less than 100 ppm by weight of carboxylic acids.

After purification and before introduction into the hydrogenation unit, the alkyl ester stream contains preferably less than 20 mol % of water, preferably less than 2 mol %, more preferably less than 0.2 mol % and most preferably the hydrogenation unit is operated in the absence of water.

According to an alternative embodiment of the present invention, water represents between 0.5 and 20 mol %, more preferably between 0.5 and 15 mol % and most preferably between 1 and 5 mol % of the total liquid feed (alkyl ester, alcohol and water) to the hydrogenation unit.

These said purification treatments are especially advantageous when a copper-based catalyst is employed in the hydrogenation unit.

Furthermore, the alkyl ester feed is preferably vapourised prior to contacting the hydrogenation catalyst, by either heating the alkyl ester in a separate vapouriser prior to having contact with the $H_2$ or, by heating the alkyl ester together with the $H_2$ (e.g. either in a separate vessel or on a pre-bed to the hydrogenation unit). The feed mixture including recycles entering the hydrogenation unit (e.g. the $H_2$ together with the alkyl esters), is preferably introduced at greater than 10° C. above its dew point temperature, and more preferably at greater than 20° C. above its dew point temperature.

According to the present invention, the alkyl esters are introduced into the hydrogenation unit together with $H_2$ to produce a stream comprising alcohols. In addition to the production of alcohols, the hydrogenation process also produces other reaction products such as alkyl esters arising from trans esterification, trace amounts of methane, ethane, water and aldehydes, together with unreacted starting materials, e.g. unreacted alkyl esters, (e.g. from recycle) and unreacted $H_2$.

For example, when methyl ethanoate is used as a feed for the hydrogenation unit, it also produces ethyl ethanoate by trans-esterification. The proportion of alkyl ester(s) present in the exit stream will be determined by the nature of the catalyst and the degree of conversion. The proportion of alkyl ester(s) may be further varied, if desired, by introducing an acidic function into the catalyst bed to promote in situ trans-esterification. The alkyl ester(s) may be recovered from the hydrogenation unit for recycle to other process stages such as the etherification unit, the carbonylation unit and/or as a recycle to the hydrogenation unit. More preferably the quantities of these fluxes are minimised.

According to a preferred embodiment of the present invention, in order to minimize the cost of separation and recycle of alkyl ester(s) within the process the hydrogenation unit is operated at high conversion of alkyl ester(s) feed to alcohol(s), such as greater than 50%, more preferably greater than 75%, more preferably still greater than 90% and most preferably greater than 95%.

It is has also been found to be an advantage of this process, that the selectivity of the alkyl ester(s) hydrogenation to alcohol(s) process can be further increased, at the expense of undesirable by-products, such as the aforementioned alkanes (e.g. ethane and methane).

Preferably, at least a part, preferably all, of the $H_2$ fed into the hydrogenation unit emanates from the synthesis gas generation procedure (i.e. it is obtained during the aforementioned $CO/H_2$ separation), where, if need be, the $H_2$ content can be further increased by subjecting the said synthesis gas to a water-gas shift reaction and a subsequent $H_2$ separation.

Alternatively the $H_2$ stream may originate from a variety of other chemical processes, including ethene crackers, styrene manufacture and catalytic reforming. However, it is known that the main commercial processes for purposeful generation of $H_2$ are autothermal reforming, steam reforming and partial oxidation of hydrocarbon feedstocks such as natural gas, coal, coke, deasphalter bottoms, refinery residues and biomass. $H_2$ may also be produced by electrolysis of water.

The overall choice of technology for producing $H_2$ is generally determined by the following economic considerations and factors:
  i. feedstock cost
  ii. feedstock availability
  iii. capital cost
  iv. local energy and operating costs; and
  v. environmental considerations The catalyst(s) employed in the hydrogenation unit is selected from any of the following:
  (i) a precious metal based catalyst, comprising of at least one noble metal from Group VIII of the periodic table (CAS version, for example iron, ruthenium, osmium, cobalt, rhodium, iridium, nickel, palladium, platinum) and at least one of the metals chosen from rhenium, tungsten and/or molybdenum; and optionally an additional metal, that is capable of alloying with said Group VIII noble metal; or
  (ii) a copper-based catalyst (for example a copper chromite or a mixed copper metal oxide-based catalyst wherein the second metal can be copper, zinc, zirconium or manganese).

According to a preferred embodiment of the present invention, the catalyst(s) employed in the hydrogenation unit is a copper-based catalyst, most preferably comprising copper and zinc. The copper-based catalyst comprising copper and zinc has a composition of copper oxide plus zinc oxide preferably greater than 75 wt %, more preferably greater than 90 wt % and most preferably greater than 95 wt %.

All of the aforementioned catalysts may advantageously be supported on any suitable support known to those skilled in the art; non-limiting examples of such supports include carbon, silica, titania, clays, aluminas, zinc oxide, zirconia and mixed oxides. Preferably, the palladium-based catalyst is supported on carbon. Preferably, the copper-based catalyst is supported on zinc oxide and preferably comprises between 20 and 40 wt % of copper.

According to a preferred embodiment of the present invention, the catalyst(s) employed is heterogeneous.

The hydrogenation process may be operated in a gas phase, or a mixed gas/liquid phase regime. The mixed gas/liquid phase regime is where the reactant mixture, at the reactor conditions, is below the dew point temperature.

The hydrogenation can be conducted in batch or semi continuous or continuous mode. Continuous mode of operation is the most preferred.

The hydrogenation reaction can be conducted in adiabatic or isothermal mode; where adiabatic mode of operation is preferred. Suitable reactors include single, or a plurality, of adiabatic bed reactors which can be used in series or parallel. For reactors utilised in series, heat exchangers and/or intercoolers and/or additional reactant and/or recycle of intermediates can be employed in between successive reactors to control the reaction temperature. The preferred adiabatic temperature rise is less than 50° C., preferably less than 25° C. and most preferably less than 10° C. The preferred use of adiabatic reactors is in series. The adiabatic reactors may be operated at different temperatures depending on composition of the individual reactor feeds.

The hydrogenation can also be conducted in multi-tubular reactors in which case a cooling/heating medium is circulated around the tubes to control the temperature. For exothermic reactions, as such, there will be a radial temperature gradient in the reactor, the preferred gradient is less than 50° C. preferably less than 25° C. most preferably less than 10° C. The preferred flow regime in this type of reactor is turbulent rather than laminar, this corresponds to a Reynolds number greater than 2100 (where the velocity is approximated by velocity in an unpacked tube).

The hydrogenation reaction can also be conducted in other reactor types such as fluidised bed, spinning basket and buss loop, heat exchanger reactors. A mixed liquid/gas phase hydrogenation reaction can be conducted with co-flow or counterflow of the $H_2$ and gas to the liquid (e.g. a bubble reactor). The preferred mode of operation of gas/liquid reactors is co-flow, also known as trickle bed operation; this can be conducted in at least one tubular and/or multi-tubular reactor in series. The hydrogenation reaction may change from a mixed gas/liquid phase to a fully gas phase reaction, as the reaction proceeds down the reactor. The mixed phase hydrogenation can also be conducted in other types of reactors, or within a combination of different reactors, for example in a slurry or stirred tank reactor with, or without, external circulation and optionally operated as a cascade or stirred tanks, a loop reactor or a Sulzer mixer-reactor.

The hydrogenation reactor(s) preferably operate at a temperature of more than 150° C., but less than 290° C.

According to a preferred embodiment of the present invention the reaction temperature is more than 150° C., preferably more than 170° C. and most preferably more than 190° C.; and less than 250° C.

The hydrogenation reaction may be operated at a pressure of more than 3 MPa, preferably at a pressure of more than 5 MPa; and at a pressure of less than 15 MPa, more preferably at a pressure less than 13 MPa and most preferably at a pressure less than 9 MPa.

According to an embodiment of the present invention, when the hydrogenation unit(s) is operated with a copper-based catalyst, the feed mixture introduced into the reactor(s) is always above its dew point temperature.

The GHSV for continuous operation may be in the range 50 to 50,000 $h^{-1}$, preferably from 1,000 to 30,000 $h^{-1}$ and most preferably from 2,000 to 9,000 $h^{-1}$.

The ester liquid substrate introduced into the hydrogenation unit preferably has an LHSV less than 10 $h^{-1}$, more preferably less than 5 $h^{-1}$ and most preferably less than 3 $h^{-1}$; for example, a typical LHSV for normal operation is approximately 1 $h^{-1}$.

For the purposes of calculating the GHSV and/or the LHSV of the present invention, when the reactors are arranged in series, said "catalyst volume" refers to the combined volume of the catalyst in all of the reactors in series.

According to a preferred embodiment of the present invention, the molar ratio of $H_2$ to alkyl ester that is introduced into the hydrogenation unit is greater than 2:1, preferably the molar ratio is greater than 4:1 and most preferably the molar ratio is greater than 5:1; and is less than 100:1, preferably less than 50:1 and most preferably less than 15:1.

According to a preferred embodiment of the present invention, the effluent exiting the hydrogenation reactor, (or the last in a train of reactors), is subjected to a separation stage, e.g. cooling the effluent and then feeding the cooled effluent to a flash vessel (wherein the said effluent can be both cooled and/or flashed several times). After this treatment, a vapour stream containing the majority of the $H_2$ and inert gases (including light alkanes; nitrogen; CO; and $CO_2$) in the effluent is recovered for recycle to the hydrogenation unit(s). The concentration of said inert gases can be controlled by diverting a proportion of the gas recycle stream to purge.

According to the present invention, the stream exiting the hydrogenation unit is then subjected to a separation stage (e.g. distillation), whereby a fraction comprising alcohol(s) is separated and recovered. Said separated and recovered alcohols comprise the following: methanol, ethanol, propanol(s) (n-propanol with low amounts of iso-propanol), butanol(s) (n-butanol and iso-butanol) and pentanol(s) and together represent the targeted alcohols (as mentioned hereinabove) of the present invention.

It should be noted that whilst all of the aforementioned temperature and pressure operating conditions form preferred embodiments of the present invention, they are not, by any means, intended to be limiting, and the present invention hereby includes any other pressure and temperature operating conditions that achieve the same effect.

The invention claimed is:

1. A process for homologation of alcohol(s), comprising the following steps:
    1 introducing alcohol(s) into an etherification unit to produce alkyl ether(s),
    2 introducing at least a part of the alkyl ether(s) from step 1, together with CO and optionally $H_2$, into a carbonylation unit, in the presence of an acidic homogeneous or heterogeneous carbonylation catalyst, to produce alkyl ester(s),
    3 introducing at least a part of the alkyl ester(s) from step 2, together with $H_2$, into a hydrogenation unit, to produce homologated alcohol(s),
    4 optionally recycling at least a part of the homologated alcohol(s) from step 3, into the etherification unit of step 1, and
    5 recovering alcohol(s) from the hydrogenation unit of step 3.

2. A process for the conversion of a carbonaceous feedstock into alcohol(s), wherein the carbonaceous feedstock is first converted into synthesis gas, which is subsequently converted into homologated alcohol(s), comprising the following steps:
    1 introducing a carbonaceous feedstock, into a synthesis gas generation unit, in order to produce a mixture of carbon oxide(s) and $H_2$ (synthesis gas),
    2 introducing at least a part of the carbon oxide(s) and $H_2$, from step 1, into an alcohol synthesis unit, to produce alcohol(s),
    3 introducing at least a part of the alcohol(s) from step 2, into an etherification unit to produce alkyl ether(s),
    4 introducing at least a part of the alkyl ether(s) from step 3, together with CO and optionally $H_2$, into a carbonylation unit, in the presence of an acidic homogeneous or heterogeneous carbonylation catalyst, to produce alkyl ester(s),
    5 introducing at least a part of the alkyl ester(s) from step 4, together with $H_2$, into a hydrogenation unit, to produce homologated alcohol(s),
    6 optionally recycling at least part of the homologated alcohol(s) from step 5, into the etherification unit of step 3, and
    7 recovering alcohol(s) from the hydrogenation unit of step 5.

3. A process according to claim 1, wherein the alcohol introduced into the etherification unit is methanol.

4. A process according to claim 1, wherein the etherification unit employs catalyst(s) selected from the group consisting of zeolites; strong acid ion exchange resins; supported heteropolyacids; and mixtures thereof.

5. A process according to claim 1, wherein the carbonylation process is performed in the presence of an acidic homogeneous or acidic heterogeneous catalyst, and is selected from the group consisting of homogeneous strong acid catalyst(s), heterogeneous analogues, heterogeneous catalysts and mixtures thereof.

6. A process according to claim 1, wherein the carbonylation process is performed in the presence of a catalyst comprising a zeolite having at least one 8-member ring channel.

7. A process according to claim 6, wherein the zeolite catalyst for use in the carbonylation process is used in the acidic form.

8. A process according to claim 6, wherein the carbonylation catalyst is composed of mordenite or ferrierite, or mixtures of the two.

9. A process according to claim 1, wherein the carbonylation process is performed under anhydrous conditions.

10. A process according to claim 1, wherein the carbonylation process is run at temperatures of from 150 to 600 ° C.

11. A process according to claim 1, wherein the hydrogenation unit employs a copper-based catalyst.

12. A process according to claim 1, wherein the alkyl ester stream entering into the hydrogenation reactor contains less than 5 wt % of carboxylic acids.

13. A process according to claim 1, wherein the alkyl ester stream entering into the hydrogenation unit contains less than 20 mol % of water.

14. A process according to claim 1, wherein the hydrogenation unit is operated at a temperature that is greater than 150° C. and less than 250° C.

15. A process according to claim 1, wherein the hydrogenation unit is operated at a pressure of greater than 1 MPa and at a pressure of less than 15 MPa.

16. A process according to claim 5, wherein the homogeneous strong acid catalyst is phosphoric acid.

17. A process according to claim 5, wherein the heterogeneous analogues are selected from the group consisting of supported phosphoric acid and SAPO's catalysts.

18. A process according to claim 5, wherein the heterogeneous catalysts are selected from the group consisting of zeolites, strong acid and ionic resins catalysts.

* * * * *